United States Patent
Hall et al.

(10) Patent No.: US 10,455,817 B2
(45) Date of Patent: Oct. 29, 2019

(54) ANIMAL OLFACTORY DETECTION OF DISEASE AS CONTROL FOR HEALTH METRICS COLLECTED BY MEDICAL TOILET

(71) Applicants: David R. Hall, Provo, UT (US); Joe Fox, Spanish Fork, UT (US); Terrece Pearman, Draper, UT (US)

(72) Inventors: David R. Hall, Provo, UT (US); Joe Fox, Spanish Fork, UT (US); Terrece Pearman, Draper, UT (US)

(73) Assignee: Hall Labs LLC, Provo, UT (US)

( * ) Notice: Subject to any disclaimer, the term of this patent is extended or adjusted under 35 U.S.C. 154(b) by 246 days.

(21) Appl. No.: 15/284,817

(22) Filed: Oct. 4, 2016

(65) Prior Publication Data

US 2018/0092335 A1    Apr. 5, 2018

(51) Int. Cl.
*A01K 29/00* (2006.01)
*A61B 5/15* (2006.01)
(Continued)

(52) U.S. Cl.
CPC ...... *A01K 29/005* (2013.01); *A61B 5/150045* (2013.01); *A61B 10/007* (2013.01); *A61B 10/0038* (2013.01); *A61B 10/0051* (2013.01); *A61B 10/0058* (2013.01); *A61B 10/0064* (2013.01); *G01N 33/0027* (2013.01); *G01N 33/483* (2013.01); *A61B 2010/0061* (2013.01);
(Continued)

(58) Field of Classification Search
CPC .............................. G01N 33/0001; E03D 9/052
See application file for complete search history.

(56) References Cited

U.S. PATENT DOCUMENTS

| 4,944,045 A | * | 7/1990 | Agelatos | ................. E03D 9/052 4/213 |
| 5,029,346 A | * | 7/1991 | Fernald, Sr. | ............ E03D 9/052 4/213 |

(Continued)

FOREIGN PATENT DOCUMENTS

EP    2545847 A1 *   1/2013   ............... A61B 5/00

OTHER PUBLICATIONS

Willis, Carolyn M., et al. "Olfactory detection of human bladder cancer by dogs: proof of principle study." Bmj 329.7468 (2004): 712.*

(Continued)

*Primary Examiner* — Jonathan M Dunlap

(57) ABSTRACT

We disclose a medical toilet that comprises one or more medical devices and a control for the metrics they collect. The medical devices may be used to collect metrics relevant to a user's health status. The medical toilet further comprises a conduit through which volatile organic compounds travel from the toilet bowl to the environment outside the toilet. An animal trained to identify the scent of bodily waste collected from a user that is afflicted with a disease perceives the scent of the user's bodily waste traveling through the conduit and performs a defined act upon perceiving the disease scent. The metric collected by the medical device(s) may be used to diagnose the same disease as that which the animal is trained to identify. The diagnosis provided by the animal by way of the conduit acts as a control for the metric collected by the medical device.

17 Claims, 11 Drawing Sheets

(51) Int. Cl.
*A61B 10/00* (2006.01)
*G01N 33/00* (2006.01)
*G01N 33/483* (2006.01)

(52) U.S. Cl.
CPC .......... *A61B 2010/0067* (2013.01); *A61B 2010/0074* (2013.01); *A61B 2010/0087* (2013.01)

(56) References Cited

U.S. PATENT DOCUMENTS

| | | | | |
|---|---|---|---|---|
| 5,073,500 | A * | 12/1991 | Saito | A61B 5/14507 4/300 |
| 5,454,122 | A * | 10/1995 | Bergeron | E03D 9/052 4/213 |
| 5,625,911 | A * | 5/1997 | Nakayama | A61B 10/007 4/661 |
| 5,720,054 | A * | 2/1998 | Nakayama | A61B 10/007 4/420 |
| 6,019,862 | A * | 2/2000 | Cardwell | C04B 37/001 156/62.2 |
| 6,088,845 | A * | 7/2000 | Estrada | E03D 9/05 4/306 |
| 6,209,146 | B1 * | 4/2001 | Gonzalez | E03D 9/05 4/209 R |
| 6,212,698 | B1 * | 4/2001 | Stingley | A61B 10/007 4/144.1 |
| 6,279,173 | B1 * | 8/2001 | Denzin | E03D 9/05 4/213 |
| 6,370,702 | B1 * | 4/2002 | Iddings, Sr. | E03D 9/05 4/213 |
| 6,496,986 | B1 * | 12/2002 | Lumsden | E03D 9/05 4/213 |
| 6,966,840 | B2 * | 11/2005 | Nelson | G08B 21/12 446/175 |
| 7,987,527 | B1 * | 8/2011 | Shumaker | E03D 9/052 4/213 |
| 8,417,304 | B2 * | 4/2013 | Onoe | A61B 5/02438 600/310 |
| 9,499,966 | B2 * | 11/2016 | Darnell | E03D 9/05 |
| 9,592,034 | B2 * | 3/2017 | Hall | A61B 10/007 |
| 9,671,343 | B1 * | 6/2017 | Hall | G01N 21/6428 |
| 2001/0031913 | A1 * | 10/2001 | Ito | A61B 5/0002 600/300 |
| 2005/0261605 | A1 * | 11/2005 | Shemer | A61B 10/007 600/573 |
| 2006/0258915 | A1 * | 11/2006 | Ueda | A47K 13/30 600/301 |
| 2007/0022522 | A1 * | 2/2007 | Yu | A47K 13/24 4/237 |
| 2007/0168229 | A1 * | 7/2007 | Kim | A61B 5/0002 705/2 |
| 2008/0256696 | A1 * | 10/2008 | Walsmley | A61B 10/0038 4/420 |
| 2009/0216099 | A1 * | 8/2009 | Kim | A61B 5/022 600/345 |
| 2016/0000378 | A1 * | 1/2016 | Hall | A61B 5/0075 702/19 |
| 2016/0220170 | A1 * | 8/2016 | Hasegawa | A61B 5/42 |
| 2016/0345539 | A1 * | 12/2016 | Mark-Danieli | A01K 1/031 |
| 2017/0204595 | A1 * | 7/2017 | Hall | E03D 9/052 |
| 2017/0242004 | A1 * | 8/2017 | Hanson | G01N 21/77 |
| 2019/0059860 | A1 * | 2/2019 | Shahaf | A47K 11/105 |

OTHER PUBLICATIONS

Bomers, Marije K., et al. "Using a dog's superior olfactory sensitivity to identify Clostridium difficile in stools and patients: proof of principle study." Bmj 345 (2012): e7396.*

Vaux, David L., Fiona Fidler, and Geoff Cumming. "Replicates and repeats—what is the difference and is it significant?: A brief discussion of statistics and experimental design." EMBO reports 13.4 (2012): Abstract.*

Cornu, Jean-Nicolas, et al. "Olfactory detection of prostate cancer by dogs sniffing urine: a step forward in early diagnosis." European urology 59.2 (2011): 197-201.*

* cited by examiner

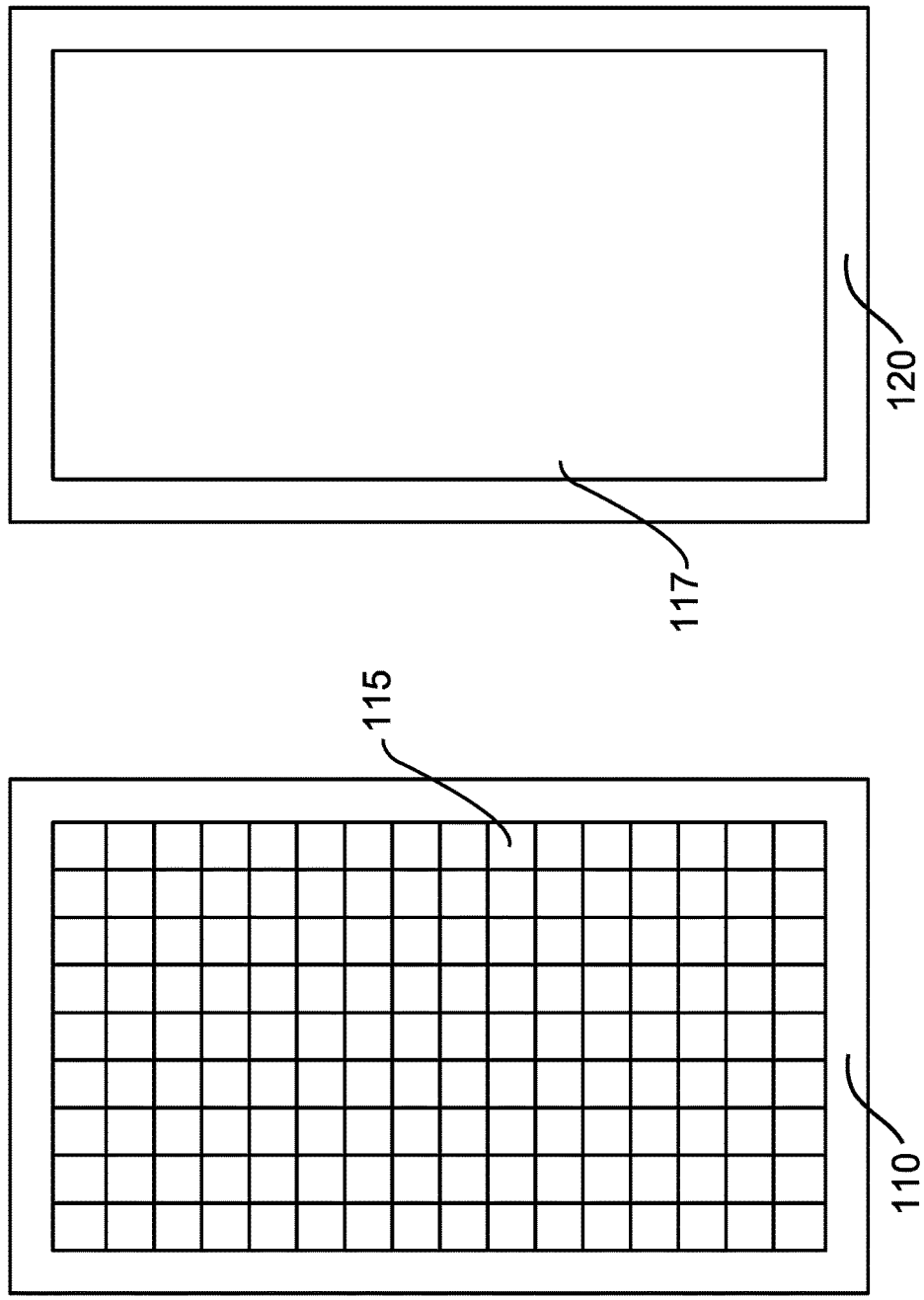

ANIMAL OLFACTORY DETECTION OF DISEASE AS CONTROL FOR HEALTH METRICS COLLECTED BY MEDICAL TOILET

BACKGROUND

Field of the Invention

This invention relates to a device for diagnosing disease and use thereof.

Background of the Invention

Many animals have heightened senses relative to humans. In fact, humans have used the relatively enhanced ability to see, hear, and smell of animals to perform tasks for hundreds of years. In particular, dogs have been used for their enhanced sense of smell to assist in tasks that include hunting, protecting livestock from predators, searching for specific humans, and detecting illegal substances. More recently, evidence has been reported that dogs have predicted seizures before they happened and identified cancer. Other organisms, including rats, mice, and insects show behavior that suggests they can identify a diseased organism.

It is unclear what substances animals smell when they identify disease. Furthermore, studies show that a variety of biological substances collected from a diseased human emit substances that animals distinguish from those of healthy humans. Reports of animals identifying disease include those in which the animal evaluated feces, urine, blood, and exhaled breath. Each of these biological substances emit volatile organic compounds (VOCs). It is likely that the biological samples the animals identify as those from a diseased human emit a plurality of different VOCs. It may be this combination that the animal perceives as the scent of disease. By smelling the combination of molecules that collectively identify disease, the animal may be able to diagnose with more sensitivity and specificity than available laboratory assays.

Furthermore, the animal's sense of smell identifies a marker of disease through a different mechanism than those employed by medical devices. Consequently, diagnosis by an animal may be a valuable method to confirm a diagnosis made through other methods.

BRIEF SUMMARY OF THE INVENTION

Every method of measuring physiological functions has inherent limitations. Medical devices may provide inaccurate results for various reasons including user error, damaged components, or attempts to use the device under conditions for which it was not designed. Consequently, it is beneficial to have a control diagnostic test to compare to a health metric collected from a medical device to confirm the result obtained from the medical device. Furthermore, it is preferable that the control diagnostic test perform the assessment of the user's health status through a different mechanism than the health metric collected by the medical device.

To address this problem, we disclose a medical toilet that includes a scent dispenser which may be used as a control diagnostic test for a health metric collected by the medical toilet. The medical toilet includes at least one medical device that measures a health metric. The health metric is a measurement that may be used to assess the user's health status and/or diagnose a disease. The medical device may measure an analyte in the user's bodily waste or some other physiological characteristic or function that is an indicator of a disease.

In addition, the medical toilet includes a scent dispenser. The scent dispenser may be positioned on a side of the medical toilet and is in communication with the toilet bowl within the medical toilet. The scent dispenser comprises a conduit through which air from within the toilet bowl may travel to the environment outside the medical toilet. When bodily waste from the user is deposited into the toilet bowl, the bodily waste emits volatile organic compounds (VOCs). An animal is positioned outside the medical toilet in the vicinity of the scent dispenser. According to the invention, the animal has been trained to differentiate the scent of VOCs that emit from bodily waste that is collected from a user with a specific disease from that collected from a user that is not afflicted with that disease. The animal performs a defined act which signals to an observer that the animal has perceived the scent of VOCs associated with the disease. The disease associated with the VOCs according to the invention is the same disease as the health metric collected by the medical device is designed to measure. Consequently, the medical device and the scent dispenser provide two methods of testing a user for a disease. The scent dispenser thus functions as a control for the health metric collected by the medical device of the medical toilet.

BRIEF DESCRIPTION OF THE DRAWINGS

FIG. 1B is a schematic view of an embodiment of the scent dispenser.

DETAILED DESCRIPTION OF THE INVENTION

Definitions

Figure 1A:
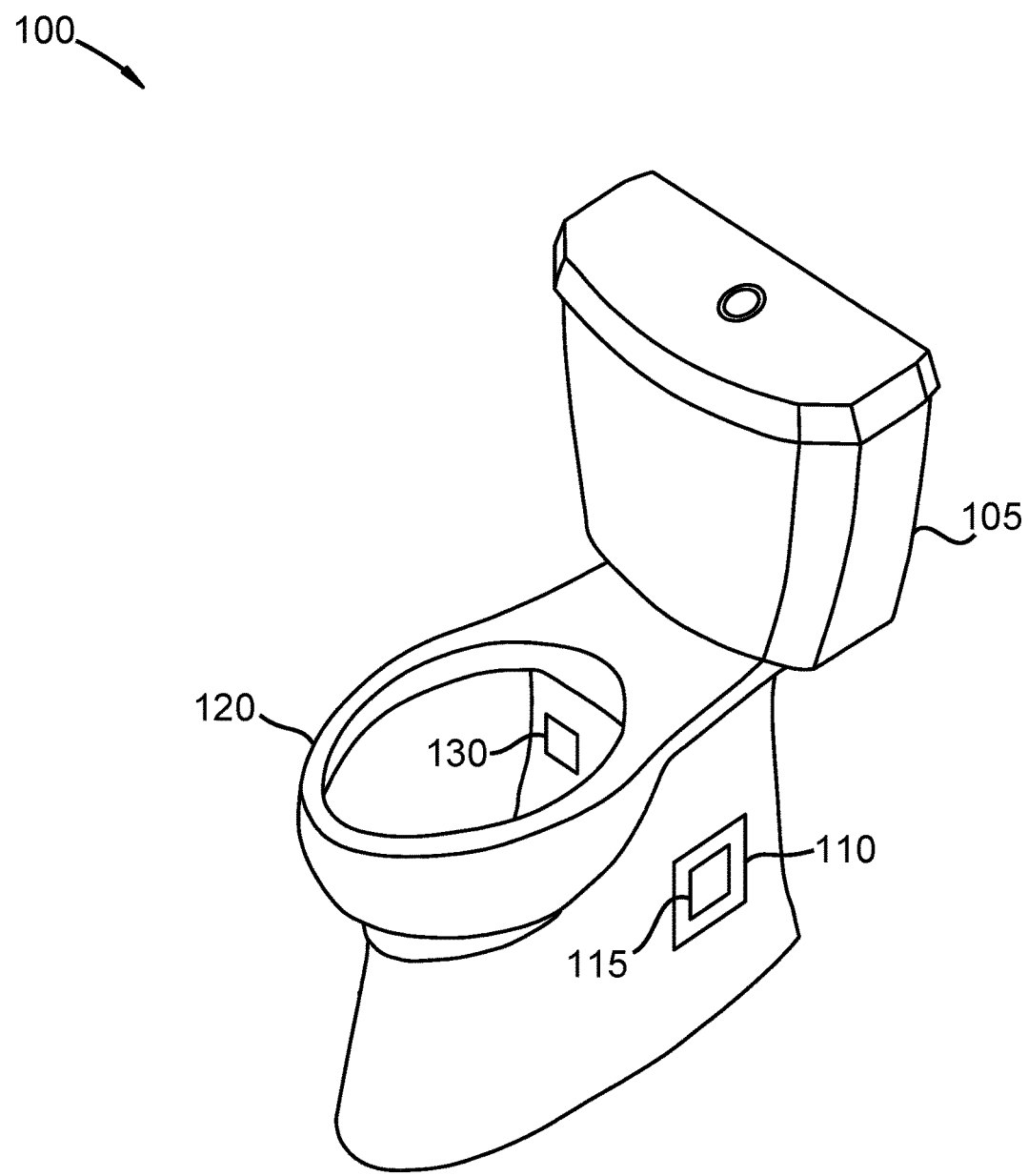
FIG. 1A is a perspective view of a medical toilet with an embodiment of the scent dispenser and a medical device within.

Toilet, as used herein, means a device that may be used to collect one or more bodily waste products of a user.

Medical toilet, as used herein, means a toilet that comprises one or more medical devices which measure physiological characteristics, physiological functions, and/or analytes within bodily waste for use in assessing a user's health status.

User, as used herein, means a human or animal that deposits bodily waste into an embodiment of the toilet disclosed herein and for which the medical toilet is used to measure physiological functions which may be used to assess the health status of the human or animal.

Healthcare provider, as used herein, means any individual who performs a task, mental or physical, in relation to health-related services provided to a user. In addition to clinicians who practice medicine directly on a user, the term healthcare provider includes any person that enters data into a computer, when the data entry is used in analysis of a user's health status or to improve a user's health.

Bodily waste, as used herein, means any one or combination of urine, feces, vomit, sputum, blood, seminal fluid, tears, nasal mucus, gastrointestinal tract mucus, urogenital tract mucus, saliva, exhaled breath, or sweat from the body of a user.

Animal, as used herein, means non-human members of kingdom Animalia, including vertebrates, invertebrates, insects, and marine organisms.

Disease, as used herein, means any disorder of structure or function in the body or a human or animal, whether or not the disorder presents with signs or symptoms.

Diseases that may be diagnosed according to the methods disclosed herein and using the medical toilet disclosed herein include, but are not limited to, colon adenoma, colon carcinoma, colon adenocarcinoma, colorectal adenoma, colorectal carcinoma, colorectal adenocarcinoma, bladder carcinoma, bladder adenocarcinoma, liver adenoma, liver carcinoma, liver adenocarcinoma, esophageal adenoma, esophageal carcinoma, esophageal adenocarcinoma, stomach adenoma, stomach carcinoma, stomach adenocarcinoma, pancreatic adenoma, pancreatic carcinoma, pancreatic adenocarcinoma, lung cancer, mouth cancer, throat cancer, inflammatory bowel disease, urinary tract infection, gastric ulcer, diabetes, hyperglycemia, hypoglycemia, impending seizure, and impending migraine.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Disclosed herein is a medical toilet, which comprises a medical device used to diagnose disease in a user. The toilet differs from those used simply to collect and dispose of urine and feces at least because it includes a scent dispenser and at least one other medical device. The scent dispenser acts as a conduit through which volatile organic compounds (VOCs) may travel from the environment inside of the toilet, for example, the toilet bowl, to the environment outside the toilet, for example, the room air.

The scent dispenser may comprise of an opening on the side of the medical toilet. Referring now to the drawings, FIG. 1A illustrates an embodiment in which the medical toilet 100 appears much like a traditional toilet with a seat 120 and tank 105. However, FIG. 1A further illustrates a medical device 130 which, in this embodiment, is within the toilet bowl. Medical device 130 may measure properties of a user's bodily waste. However, one of skill in the art will understand that other embodiments may include a medical device positioned elsewhere in or on the medical toilet and may measure other physiological characteristics and/or functions.

FIG. 1A further illustrates an embodiment of a scent dispenser on toilet 100 which comprises a frame 110 surrounding a porous material 115. Frame 110 surrounds porous material 115 which may be constructed of a screen through which air and accompanying VOCs may travel. FIG. 1B illustrates an embodiment of a scent dispenser in greater detail.

For use in diagnosis of disease, an animal is positioned in the vicinity of the toilet and a user deposits bodily waste into the toilet bowl. A blower may be activated through mechanisms known in the art which include the use of motion sensors which would cause a signal to be transmitted to the blower when bodily waste passes by the sensor. Alternatively, the user, or possibly even the animal, may turn the blower on or off by pressing a button or flipping a switch.

The user deposits bodily waste into the toilet through actions which include urinating or defecating into the toilet, vomiting into the toilet, coughing up sputum into the toilet, and depositing mucus into the toilet. A user may deposit nasal mucus and sputum into the toilet by coughing or blowing the user's nose into a tissue and tossing the tissue into the toilet.

An animal may be trained to sniff the scent dispenser in response to a command or signal. The user may give the animal the command or signal when the user desires the animal to assess the presence of disease in the user. Alternatively, the animal may simply be trained that the scent dispense is something that the animal should sniff and do so when placed in the proximity of the toilet. Furthermore, the animal may be an insect that is placed in a container. The container may be attached to or placed in the vicinity of the scent dispenser avoiding any need to train the animal to approach the scent dispenser.

The animal must also be trained to identify a disease by the smell of bodily waste collected from a user who has that disease and to differentiate this from scents emitted by bodily waste collected from users who do not have the disease. Furthermore, the animal must be trained to perform a behavior that functions as a signal that the animal has detected the scent of disease in the user's bodily waste. Various methods of training an animal to identify a sent emanating from bodily waste that was obtained from a diseased organism as well as methods to train the animal to provide a signal to communicate upon perceiving this particular scent are known in the art and within the scope of the methods disclosed herein.

According to the invention, the disease which the health metric collected by the medical device is designed to diagnose and that which is diagnosed when the animal responds to a scent coming through the scent dispenser are the same or similar. For example, the medical device may collect a health metric from a user's urine which is an indicator of bladder cancer. The animal may also be trained to respond to a scent it perceives when sniffing VOC's that are associated with bladder cancer. Consequently, both the medical device and the scent dispenser are used to test for the presence of bladder cancer in the user. While the health metric may be a quantitative assay conducted by measuring a known analyte, the response from the animal is a qualitative assessment which is used as a control for the quantitative health metric. Both methods answer the same question through different methods. The animal and scent dispenser, thus, provide a control diagnostic technique for the health metric which is not impacted by any defect in the medical device.

In another embodiment, the medical device collects a health metric by measuring a property of a different physiological function or different type of biological sample than the bodily waste assessed by the animal. For example, the medical device on the medical toilet may perform an electrocardiogram (EKG) measurement to assess the user's cardiovascular health. The bodily waste deposited in the toilet may emit VOCs that are indicative of myocardial damage and which the animal is trained to recognize. In this embodiment, the scent dispenser and animal provide a diagnosis based on the user's bodily waste and act as a control for a health metric that is performed on the user's heart function.

FIG. 1B illustrates an embodiment of a scent dispenser. This embodiment of the scent dispenser comprises a porous material 115 surrounded by frame 110. Porous material 115 may comprise of a screen with holes of a size that allow VOCs to escape from behind the screen but protect blotting sheet 117 from damage that might occur, for example, from the animal's nose touching blotting sheet 117.

Frame 110 surrounds the perimeter of porous material 115 and may be constructed from metal, porcelain, rubber or rubberized materials, plastics that comprise of any of a variety of polymers and copolymers known in the art, glass, silicone, and ceramic. Frame 110 may be constructed of any of a variety of materials that are water resistant so as to not be damaged by exposure to toilet water. Frame 110 may include a gasket constructed of one or more of rubber, rubberized material, plastics that comprise of any of a variety of polymers and copolymers known in the art, or other materials known to prevent liquid leakage.

FIG. 1B further illustrates blotting sheet 117. Frame 120 surrounds the perimeter of blotting sheet 117. Blotting sheet 117 may comprise of any absorbent material, including but not limited to, paper, cotton, polyester, hemp, bamboo, modal fabric, and polyamide. As one of skill in the art will readily understand, any material that absorbs liquid and allows VOCs to escape from the material may be used to manufacture blotting sheet 117.

Frame 110 may be constructed to receive and hold frame 120, frame 120 being in combination with blotting sheet 117, such that blotting sheet 117 is positioned behind porous material 115. In one embodiment, frames 110 and 120 are constructed so that frame 120 is a cassette that slides laterally to a position within frame 110 fits within frame 110.

Blotting sheet 117 may be positioned within the medical toilet, such that toilet water or other solvent comes in physical contact with at least a part of blotting sheet 117 when a user has deposited bodily waste into the toilet. Alternatively, blotting sheet 117 may be positioned such that liquid bodily waste comes directly in physical contact with blotting sheet 117 without being diluted by solvent. For example, the user's urine stream may come in contact with blotting sheet 117.

In either scenario, blotting sheet 117 wicks the solution or liquid bodily waste so that it is spread across blotting sheet 117. VOCs evaporate into the environment outside the toilet, traveling through porous material 115. The animal is then able to smell the VOCs to assess them for the disease scent.

Figure 2:
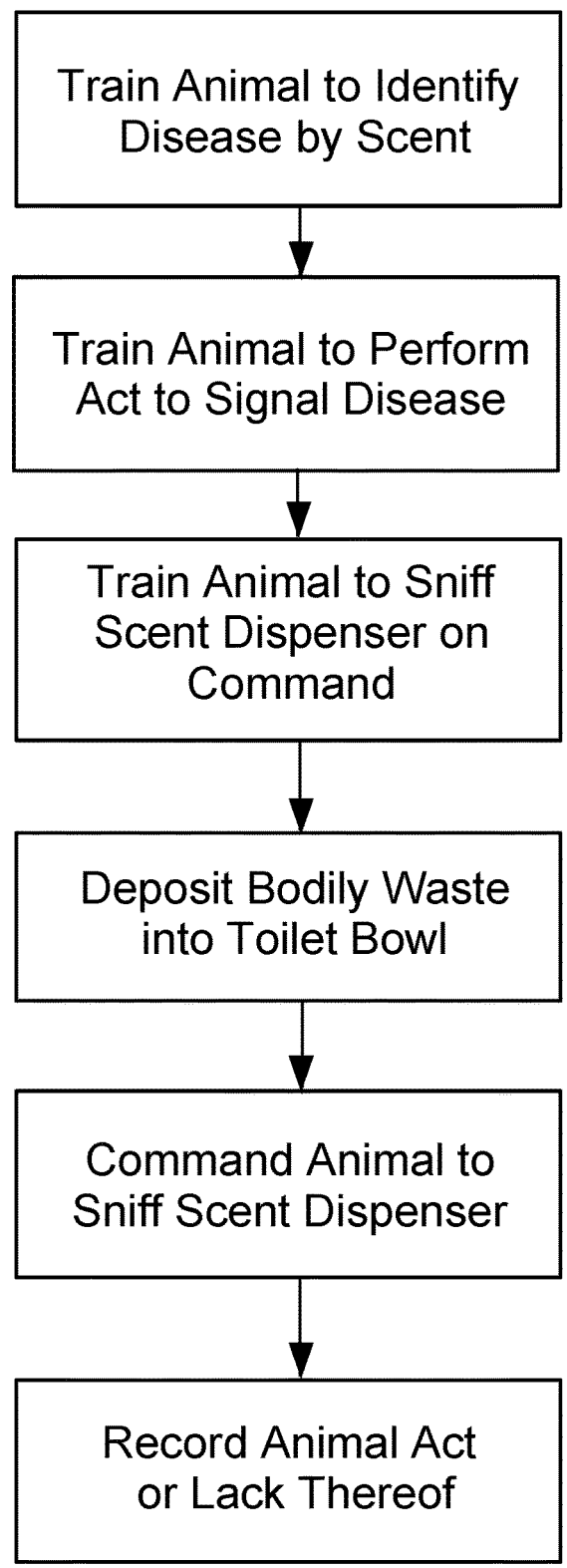
FIG. 2 is a flow chart of a method of using the scent dispenser feature of an embodiment of the medical toilet.

FIG. 2 is a flow chart that illustrates an embodiment of a method of using the animal and scent dispenser disclosed herein. In this embodiment, the animal is first trained to identify bodily waste collected from a user and differentiate it from bodily waste collected from a user that does not suffer from the disease. The animal may also be trained to perform a defined act upon perceiving the scent associated with the disease. Next the animal is trained to sniff the scent dispenser on command. The animal is now ready to participate in diagnosis of a user. Not that in some embodiments, the step of, training to sniff the scent dispenser on command may not be necessary. The animal is then brought to the medical toilet and a user's bodily waste is deposited into the toilet. The animal is given the command to sniff the scent dispenser after which the animal may perform the defined act that indicates the animal's perception of the scent associated with the disease. If the animal does not perceive the scent associated with the disease, it will not perform the defined act. Finally, the animal's response may be recorded and reported to a health care provider.

Figure 3:
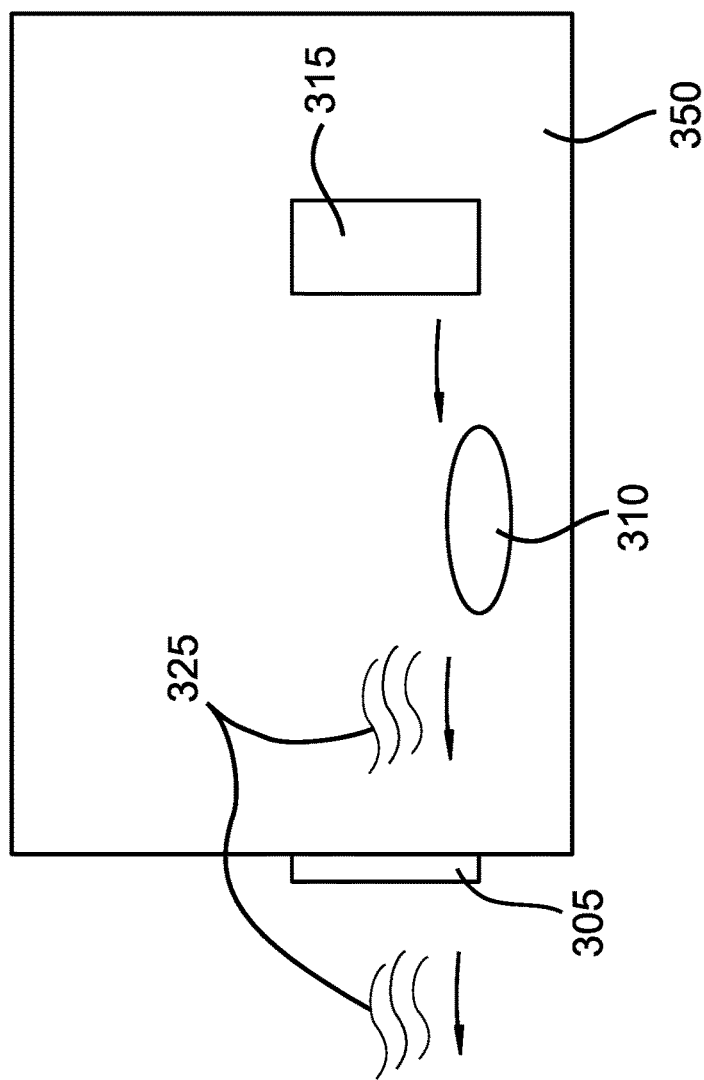
FIG. 3 is a schematic drawing of an embodiment of the medical toilet.
Figure 3:
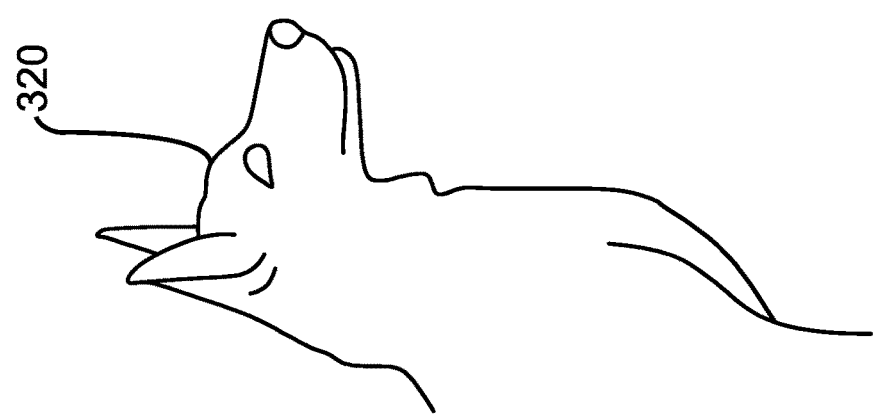

FIG. 3 illustrates one embodiment of the medical toilet, a scent dispenser, and its use with an animal. In this embodiment, animal 320 is a dog, although the animal may be another species in other embodiments. Toilet bowl 350 is drawn schematically as a rectangle. Bodily waste sample 310 is schematically represented by an elliptical shape. Bodily waste sample 310 is positioned between blower 315 and scent dispenser 305. When blower 315 is actuated, air moves from blower 315 toward scent dispenser 305 as indicated by the solid arrows. This arrangement results in VOCs 325 emitted from bodily waste sample 310 being driven, along with the air, toward scent dispenser 305. VOCs 325 travel through scent dispenser 305 to the environment outside the toilet. There, animal 320 may perceive the scent of VOCs 325.

Figure 4A:
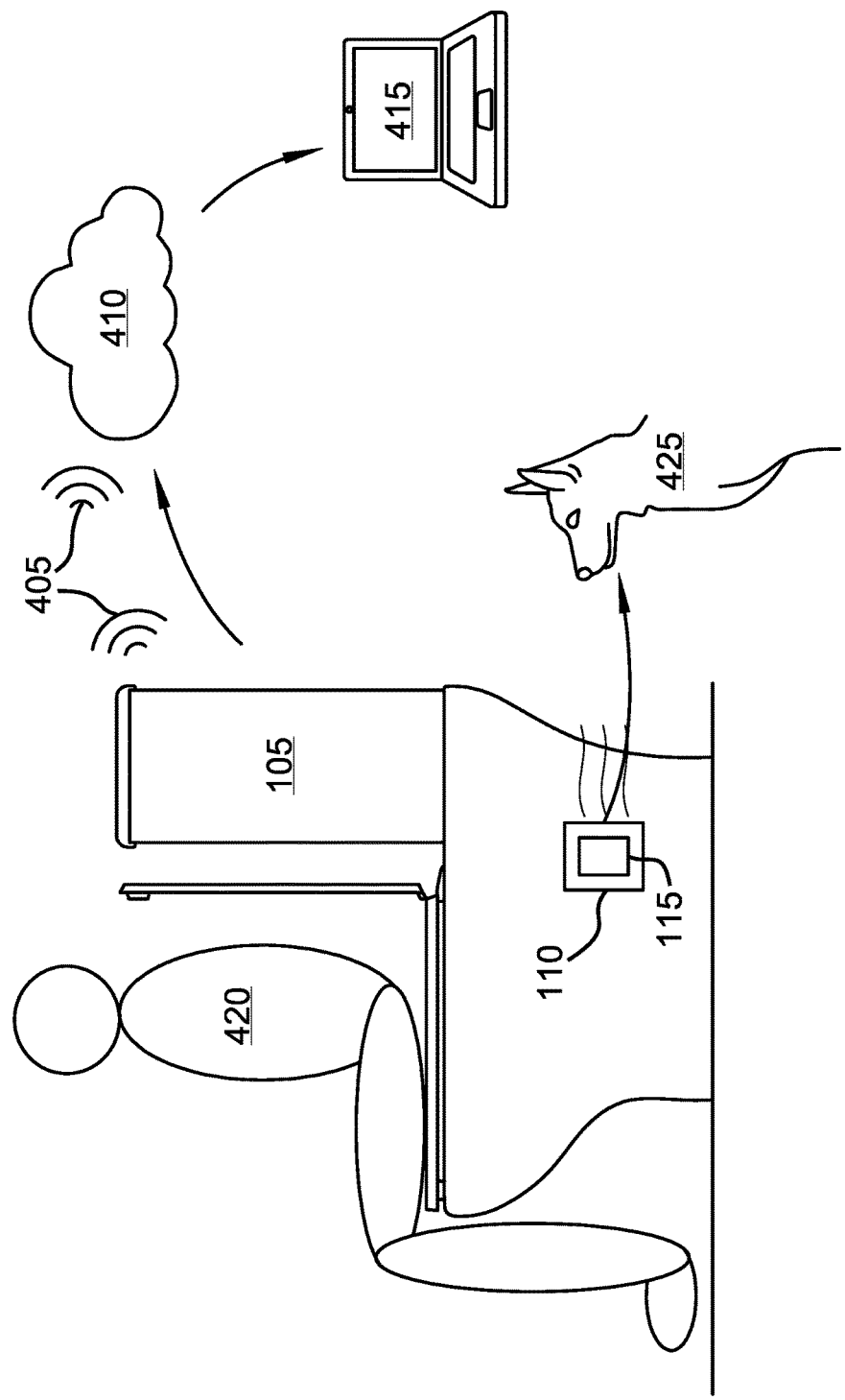
FIG. 4A is a schematic drawing of a user conducting measurements with an embodiment of the medical toilet.

FIG. 4A illustrates an embodiment of the medical toilet, in which user 420 is positioned on the seat of the medical toilet. This embodiment includes a sent dispenser similar to that of FIGS. 1A and 1B. In this embodiment, the health metric collected by the medical device within the medical toilet is transmitted to network database 410 through signal 405. The health metric may be transferred to network database 410 through wireless transmission, an Ethernet, or other methods known in the art. The health metric is then downloaded to computer 415 for analysis by a healthcare provider.

In the embodiment of FIG. 4A, user 420 has deposited bodily waste into the medical toilet and animal 425 is shown sniffing VOCs emanating from an embodiment of the scent dispenser. The bodily waste may be urine or feces in this embodiment. The medical device may be measuring an analyte in the bodily waste that is an indicator of the same disease that animal 425 is trained to associate with a specific scent.

Figure 4B:
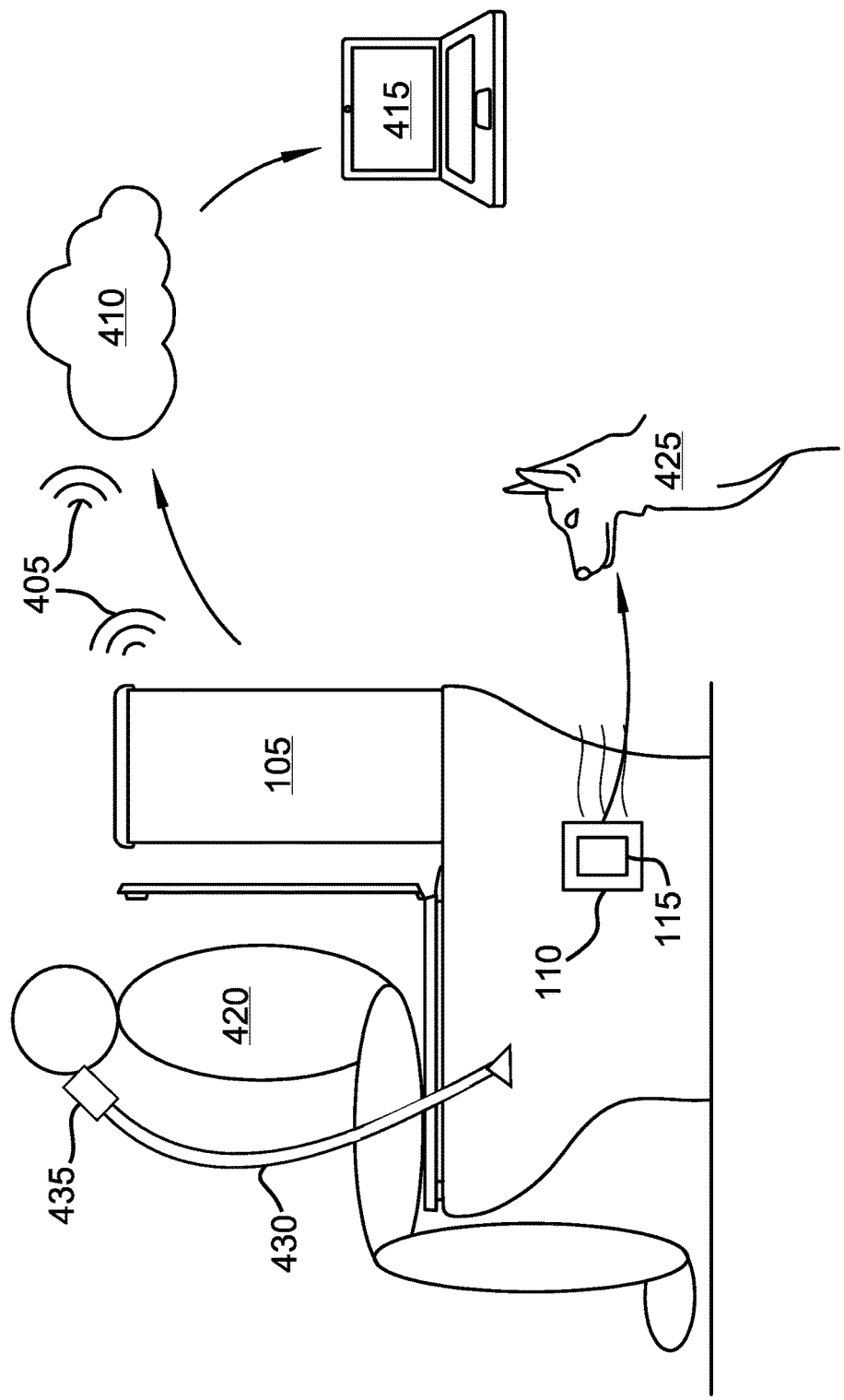
FIG. 4B is a schematic drawing of user conducting measurements with an embodiment of the medical toilet.

Alternatively, the medical device may be measuring a health metric that is not collected from the bodily waste. FIG. 4B illustrates yet another embodiment of the medical toilet which incorporates the scent dispenser of FIG. 4A. In this embodiment, the medical toilet measures a health metric that is not a measurement taken from the same bodily waste that the animal and scent dispenser analyze. As with other embodiments, the health metric is designed to diagnose the same disease as the scent dispenser and animal 425. In this embodiment, the bodily waste that emits the VOCs is the breath of user 420. User 420 exhales into mouthpiece 435 which is in communication with tubing 430. The VOCs emitted in the exhaled gasses travel through tubing 430 and out through the scent dispenser. Animal 425 perceives the scent of the VOCs. The health metric compared to the diagnosis from animal 425 and the scent dispenser may be urine, feces, or some other metric that does not involve analysis of bodily waste including tidal volume taken from a spirometer.

Figure 5:
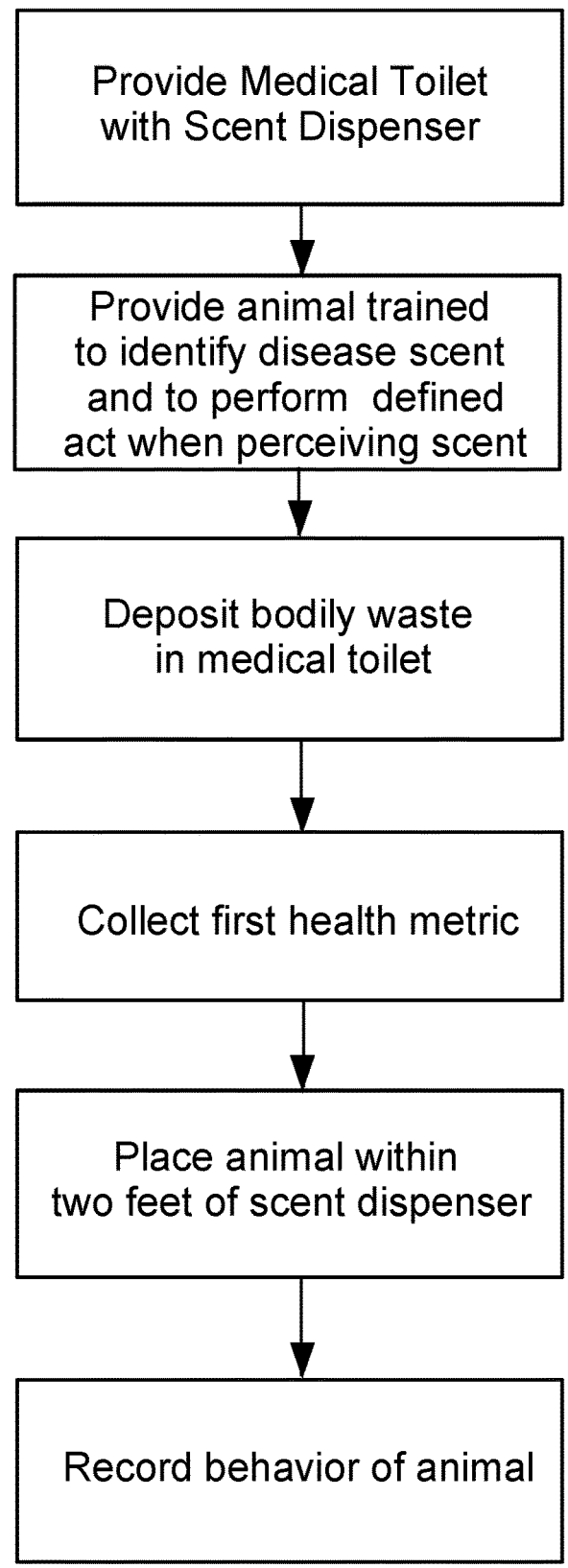
FIG. 5 is a flow chart illustrating a method of using the scent dispenser feature of an embodiment of the medical toilet as a control for another health metric.

FIG. 5 is a flow chart that illustrates a method of using the medical toilet with use of the scent dispenser as a control. In this method, the first step is to provide a medical toilet that includes a medical device capable of collecting a health metric that may be used to diagnose a disease. The medical toilet may also include a scent dispenser as described herein.

Next, an animal that is trained to identify disease by the scent of VOCs emitted from bodily waste is provided. The animal is also trained to perform a defined act upon perceiving the scent associated with the disease. The user then deposits bodily waste into the toilet. The medical device collects the health metric. Although the embodiments illustrated herein refer to a single medical device which collects a single health metric, the medical toilet may comprise of a plurality of medical devices which may collect a plurality of health metrics. Provided that the plurality of health metrics is diagnostic or suggestive of the same disease that the animal is trained to identify by scent, the scent detector and animal may be used as a control according to the disclosed invention.

In the method of FIG. 5, the animal is placed within two feet of the scent dispenser in order to perceive the scent of the VOCs emanating from the scent dispenser without distraction from smells originating from other sources. However, one of skill in the art will recognize that the distance from the scent dispenser will vary with the animal and its capabilities as well as the strength of the scent. The behavior of the animal is then recorded. The animal may perform the defined act which indicates that the animal has perceived the scent associated with the disease. Alternatively, the animal may not perform the defined act which is a signal that the animal has not perceived the scent. The result from the animal's diagnosis and that indicated by the health metric are then compared.

Figure 6A:
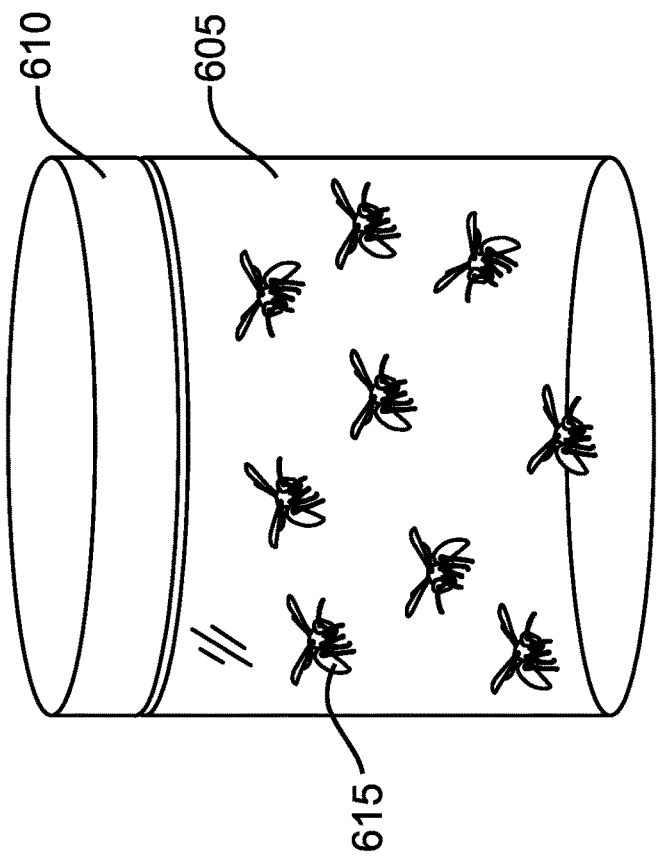
FIG. 6A is a canister containing insects, the canister being a part of an embodiment of the invention.

While FIGS. 3, 4A, and 4B illustrate a dog as the animal, FIG. 6A illustrates an embodiment in which insects 615 identify the scent associated with bodily waste collected from a diseased user. FIG. 6A illustrates container 605 which may be a canister or other enclosure that will contain live insects. One end of container 605 includes attachment device 610 which functions similar to frame 110 of FIG. 1B. Attachment device 610 may include a porous material that covers the end of container 605 and allows VOCs 325 to enter container 605. Insects 615 smell VOCs as they enter container 605. Like the embodiment in which the animal comprises a dog, insects 615 have been trained to differentiate between the scent of bodily waste from a user that is afflicted with a disease from bodily waste from a user that is not afflicted with the disease. Also, insects 615 respond by performing a defined act that signals to an observer when insects 615 have perceived the scent associated with the disease.

Figure 6B:
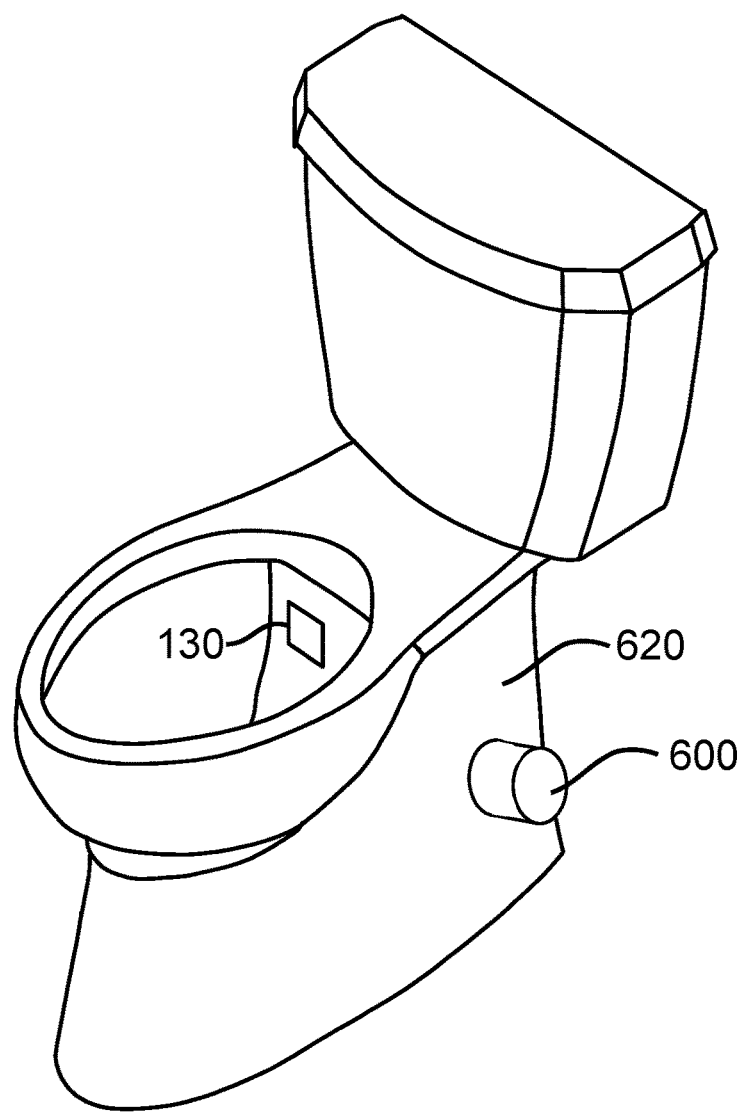
FIG. 6B is a perspective view of a medical toilet with the canister of FIG. 6A mounted on the medical toilet.

FIG. 6B illustrates the container 605 of FIG. 6A as it appears when attached to toilet 620 which is an embodiment of the medical toilet disclosed herein. Similar to other embodiments of the scent dispenser, container 605 attaches to toilet 620 on a side of toilet 620. Container 605 is in communication with the toilet bowl of toilet 620.

Figure 7:
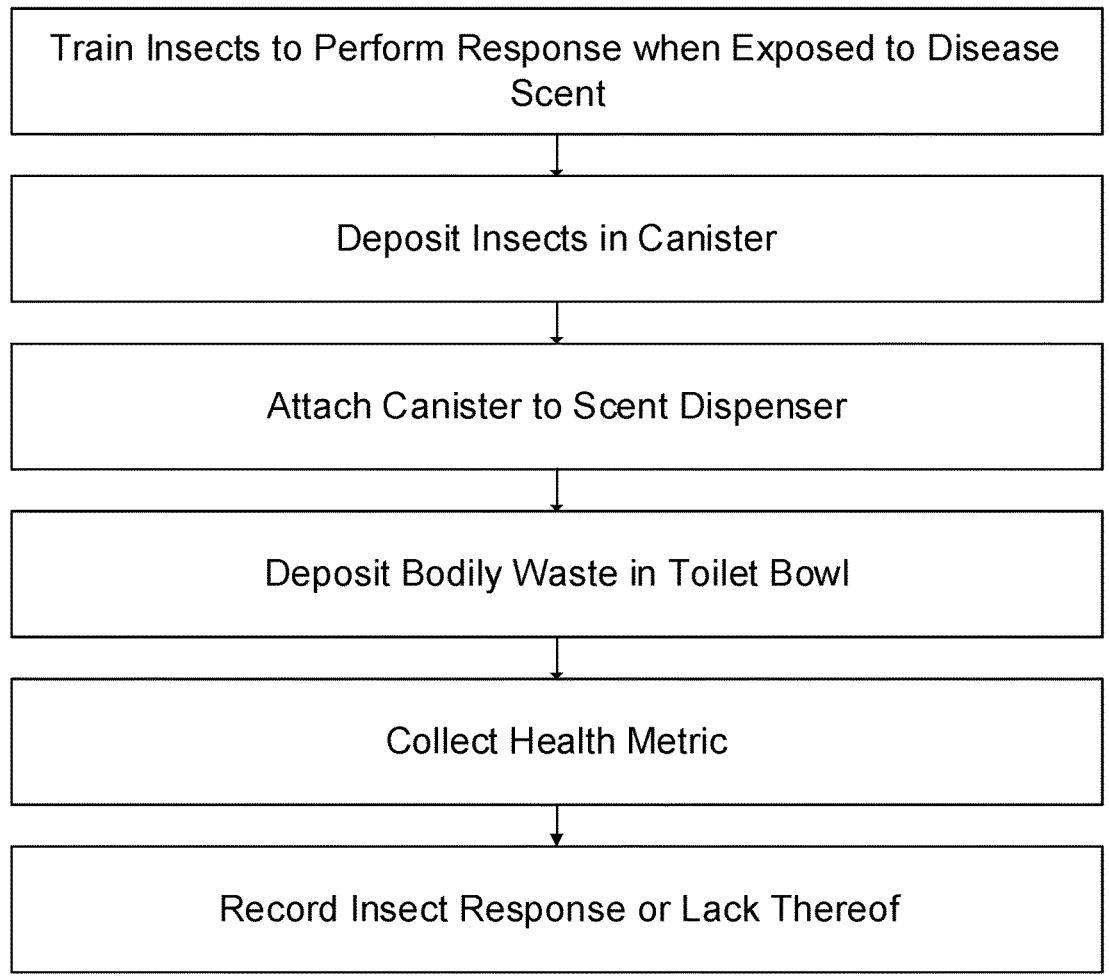
FIG. 7 is a flow chart illustrating a method of using the scent dispenser feature of an embodiment of the medical toilet as a control for another health metric.

FIG. 7 is a flow chart that illustrates an embodiment of a method in which container 605 and insects 615 may be used in accordance with the disclosed invention. Insects 605 may be trained to perform a defined act/response when they are exposed to the scent of bodily waste that was collected from a user afflicted with a disease. The defined act may comprise of one or more of vibrating, extending a proboscis, increased movement, emitting a sound whether or not the sound is audible by the human ear. One of skill in the art will understand that other insect behaviors may indicate perception of the disease scent by the insects. The insects are deposited into a canister and the canister attached to the scent dispenser on the medical toilet. A user deposits bodily waste into the medical toilet and the VOCs from the bodily waste travel through the scent dispenser and into the canister housing the insects. In this embodiment, the health metric is collected at this point in the process. The behavior of the insects is then recorded. As discussed above, performance of the defined behavior is an indication that the insects have perceived the scent associated with the disease. Alternatively, nonperformance is an indication that the insects have not perceived the scent associated with the disease. As with the embodiment illustrated in FIG. 5, the steps of FIG. 7 are performed in association with the collection of a health metric which measures an indicator of the same disease to which the insects are trained to respond.

With regard to the embodiments illustrated by the flow charts of FIGS. 5 and 7, one of skill in the art will recognize that the health metric may be collected before, during, or after the animal perceives the scent through the scent dispenser. In fact, the user may deposit the bodily waste into the medical toilet and conduct the steps in which the animal perceives the scent and responds accordingly on a different day that the first metric is collected. In embodiments in which the health metric detects the presence of an analyte in bodily waste, it is within the scope of the invention for a user to deposit a first bodily waste sample into the medical toilet for analysis by the medical device as represented by the health metric and to deposit a second bodily waste sample into the medical toilet for assessment by the animal. For example, the first bodily waste sample and the second bodily waste sample may represent different fecal samples. These different fecal samples may be produced when the user evacuates his or her bowels on different days.

Figure 8:
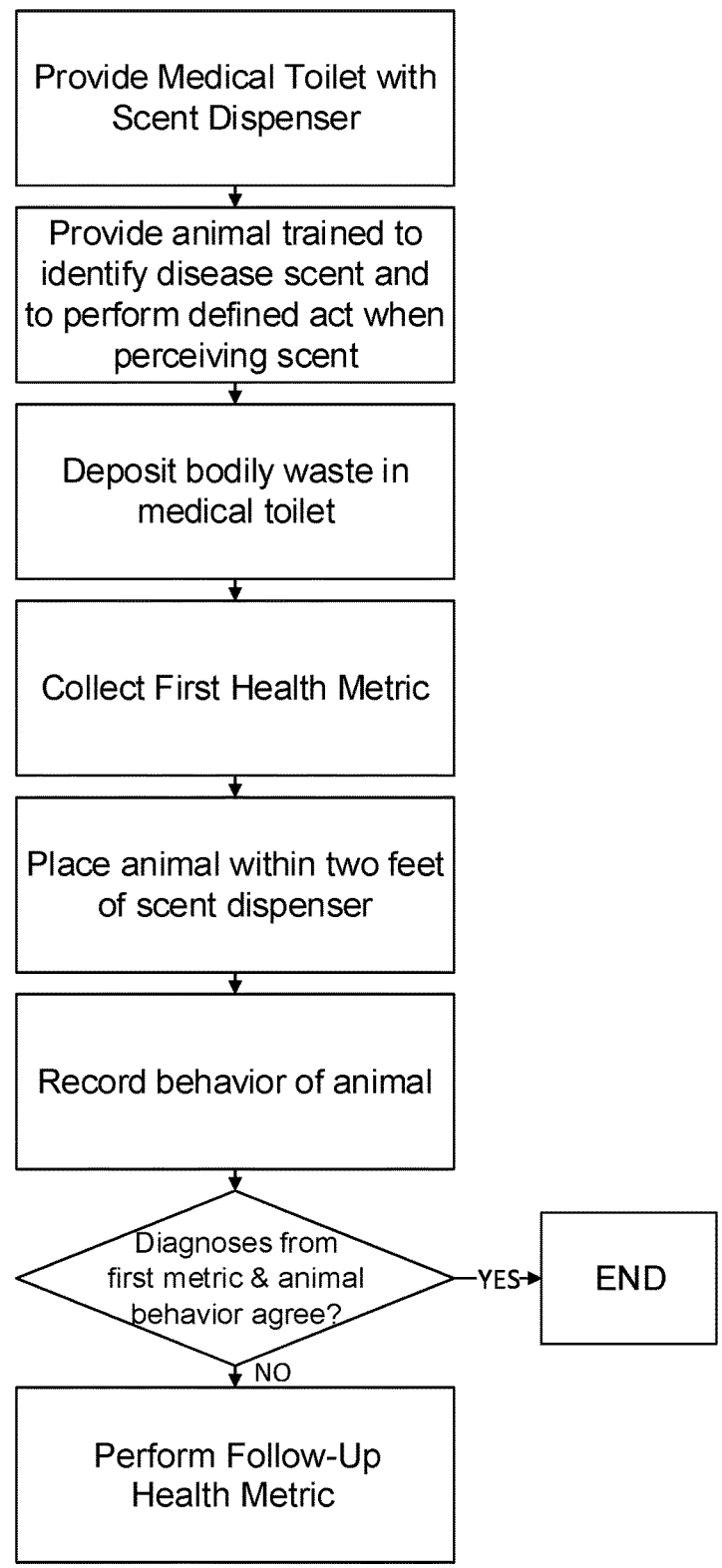
FIG. 8 is a flow chart illustrating a method of using the scent dispenser feature of an embodiment of the medical toilet as a control and with a follow-up metric.

FIG. 8 is a flow chart illustrating a method according to the disclosed invention in which the scent dispenser act as a control and in which a follow-up metric may be collected in instances in which the first metric and the scent dispenser/animal do not produce the same diagnosis. As with other embodiments disclosed herein, the method begins with the steps of providing a medical toilet that comprises a scent dispenser and providing an animal trained to identify a disease scent and perform a defined act upon perception of the disease scent. The user then deposits bodily waste into the medical toilet which emits VOCs that travel through the scent dispenser to the animal. A health metric is collected using a medical device associated with the medical toilet. In this embodiment, the animal is placed within two feet of the scent dispenser so as to perceive the scent of the VOCs. The animal's behavior is recorded whether it be performance of the defined act or lack thereof. In this embodiment, the question is asked whether or not the diagnosis obtained from the health metric and that from the scent dispenser and animal are in agreement. If they are in agreement, the health metric may be presumed to be valid. If the two diagnoses do not agree, a follow-up metric is performed to distinguish between the two diagnoses. The follow-up metric may be conducted using the medical toilet or with an alternative method.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of providing a control for a first health metric collected by a medical toilet for use in diagnosing a disease in a user comprising the steps of:
   providing a medical toilet, the toilet comprising:
      a toilet bowl;
      a toilet seat;
      a medical device which measures a first health metric, wherein the first health metric is an indicator of the disease in a user;
      a scent dispenser, the scent dispenser comprising:
         an opening within a side of the toilet;
            wherein the opening is defined by a frame, the frame comprising a first side in communication with an environment outside the toilet bowl and a second side in communication with an environment inside the toilet bowl;
            wherein the opening connects the environment inside the toilet bowl with the environment outside the toilet bowl; and
            wherein the opening defines a conduit to transfer volatile organic compounds from the toilet bowl to the environment outside the toilet;
   providing an animal, wherein the animal is trained to:
      smell the air being emitted from the scent dispenser;
      identify a scent that is associated with the disease; and
      perform a defined act when the animal perceives scent associated with the disease; and
   depositing one or more types of bodily waste from the user into the medical toilet, wherein the bodily waste emits one or more volatile organic compound;
   collecting the first health metric using the medical device of the medical toilet;
   placing the animal proximate to the scent dispenser; and
   recording the behavior of the animal which comprises either performance or nonperformance of the defined act;
   wherein the first health metric measured by the medical device and the scent identified by the animal are indicators of the same disease;
   wherein the medical device collects a first health metric by measuring a property of a different physiological function of the disease than the bodily waste that the animal and scent dispenser analyses;
   wherein the medical device provides a quantitative assessment of the disease and the animal provides a control by providing a qualitative assessment of the disease.

2. The method of claim 1, wherein the bodily waste comprises one or more of the following: urine, feces, vomit, sputum, blood, seminal fluid, tears, nasal mucus, gastrointestinal tract mucus, urogenital tract mucus, saliva, exhaled breath, or sweat.

3. The method of claim 1, further comprising collection of a follow-up health metric, wherein the follow-up health metric measures an indicator of the disease.

4. The method of claim 3, wherein the follow-up health metric is performed when the first health metric and the behavior of the animal indicate conflicting diagnosis of the disease in the user.

5. The method of claim 1, wherein a follow-up health metric comprises a measurement of an analyte present in or emitted from the one or more types of bodily waste.

6. The method of claim 1, wherein the disease is selected from one or more of the following:
   colon adenoma, colon carcinoma, colon adenocarcinoma, colorectal adenoma, colorectal carcinoma, colorectal adenocarcinoma, bladder carcinoma, bladder adenocarcinoma, liver adenoma, liver carcinoma, liver adenocarcinoma, esophageal adenoma, esophageal carcinoma, esophageal adenocarcinoma, stomach adenoma, stomach carcinoma, stomach adenocarcinoma, pancreatic adenoma, pancreatic carcinoma, pancreatic adenocarcinoma, lung cancer, mouth cancer, throat cancer, inflammatory bowel disease, urinary tract infection, gastric ulcer, diabetes, hyperglycemia, hypoglycemia, impending seizure, and impending migraine.

7. The method of claim 1, wherein the disease consists of cancer.

8. The method of claim 1, wherein the defined action is selected from one or more of the following:
   emitting a sound, tail wagging, assuming a sitting position, assuming supine position, pointing, tapping the scent dispenser with the animal's nose, tapping the scent dispenser with the animal's paw, tapping a human with the insect's or rodent's nose, tapping a human with the animal's paw, moving in circles, raising a proboscis, and vibrating.

9. A method of diagnosing a disease in a user, wherein the disease is associated with a disease process that causes the user to excrete bodily waste comprising at least one volatile organic compound that is not detectable by smell in bodily waste collected from a user not afflicted with the disease, the method comprising the steps of:
   providing a medical toilet, the medical toilet comprising:
      a toilet bowl, the toilet bowl housing a volume of toilet water;
      a toilet seat;
      a medical device, wherein the medical device collects a first health metric to identify the presence of a disease in a user;
      a scent dispenser, the scent dispenser comprising:
         an opening within a side of the medical toilet;
            wherein the opening is defined by a frame, the frame comprising a first side in communication with an environment outside the toilet bowl and a second side in communication with an environment inside the toilet bowl;
            wherein the opening connects the environment inside the toilet bowl with the environment outside the toilet bowl; and
            wherein the opening defines a conduit to transfer volatile organic compounds from the environment inside toilet bowl to the environment outside the toilet;
   providing an insect or rodent, wherein the insect or the rodent is trained to:
      identify a scent that is associated with the disease; and
      perform a defined act when the insect or the rodent perceives the scent associated with the disease;
   depositing one or more types of bodily waste from the user into the medical toilet, wherein the bodily waste emits one or more volatile organic compounds;
   collecting the first health metric using the medical toilet;
   placing the insect or the rodent proximate to the scent dispenser; and
   recording the behavior of the insect or the rodent which comprises either performance or nonperformance of the defined act;

wherein the first health metric measured by the medical device and the scent identified by the animal are indicators of the same disease;

wherein the medical device collects a first health metric by measuring a property of a different physiological function of the disease than the bodily waste that the animal and scent dispenser analyses;

wherein the medical device provides a quantitative assessment of the disease and the animal provides a control by providing a qualitative assessment of the disease.

10. The method of claim 9, wherein the bodily waste comprises one or more of the following: urine, feces, vomit, sputum, blood, seminal fluid, tears, nasal mucus, gastrointestinal tract mucus, urogenital tract mucus, saliva, exhaled breath, or sweat.

11. The method of claim 9, further comprising collection of a follow-up health metric, wherein the follow-up health metric measures an indicator of the disease.

12. The method of claim 11, wherein the follow-up health metric is performed when the first health metric and the behavior of the animal indicate a conflicting diagnosis of the disease in the user.

13. The method of claim 9, wherein a follow-up health metric comprises the measurement of an analyte present in or emitted from the one or more types of bodily waste.

14. The method of claim 9, wherein the disease is selected from one or more of the following:

colon adenoma, colon carcinoma, colon adenocarcinoma, colorectal adenoma, colorectal carcinoma, colorectal adenocarcinoma, bladder carcinoma, bladder adenocarcinoma, liver adenoma, liver carcinoma, liver adenocarcinoma, esophageal adenoma, esophageal carcinoma, esophageal adenocarcinoma, stomach adenoma, stomach carcinoma, stomach adenocarcinoma, pancreatic adenoma, pancreatic carcinoma, pancreatic adenocarcinoma, lung cancer, mouth cancer, throat cancer, inflammatory bowel disease, urinary tract infection, gastric ulcer, diabetes, hyperglycemia, hypoglycemia, impending seizure, and impending migraine.

15. The method of claim 9, wherein the disease consists of cancer.

16. The method of claim 9, wherein the defined act is selected from one or more of the following: emitting a sound, tail wagging, assuming a sitting position, assuming supine position, pointing, tapping the scent dispenser with the animal's nose, tapping the scent dispenser with the animal's paw, tapping a human with the animal's nose, tapping a human with the animal's paw, moving in circles, raising a proboscis, and vibrating.

17. A method of providing a control for a first health metric collected by a medical toilet for use in diagnosing a disease in a user comprising the steps of:

providing a medical toilet, the toilet comprising:
  a toilet bowl;
  a toilet seat;
  a medical device which measures an analyte in the bodily waste of a user to obtain a first health metric, wherein the first metric is an indicator of the disease in a user;
  a scent dispenser, the scent dispenser comprising:
    an opening within a side of the toilet;
      wherein the opening is defined by a frame, the frame comprising a first side in communication with an environment outside the toilet bowl and a second side in communication with an environment inside the toilet bowl;
      wherein the opening connects the environment inside the toilet bowl with the environment outside the toilet bowl; and
      wherein the opening defines a conduit to transfer volatile organic compounds from the toilet bowl to the environment outside the toilet;

providing an animal, wherein the animal is trained to:
  smell the air being emitted from the scent dispenser;
  identify a scent that is associated with the disease; and
  perform a defined act when the animal perceives scent associated with the disease; and depositing one or more types of bodily waste from the user into the medical toilet, wherein the bodily waste emits one or more volatile organic compound;

collecting the first health metric by measuring an analyte in the bodily waste of a user using the medical toilet;

placing the animal proximate to the scent dispenser; and recording the behavior of the animal which comprises either performance or nonperformance of the defined act;

wherein the first health metric measured by the medical device and the scent identified by the animal are indicators of the same disease.

* * * * *